(12) United States Patent
Akagane

(10) Patent No.: US 9,693,793 B2
(45) Date of Patent: Jul. 4, 2017

(54) ULTRASONIC PROBE AND ULTRASONIC TREATMENT INSTRUMENT

(71) Applicant: OLYMPUS CORPORATION, Hachioji-shi, Tokyo (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/259,573

(22) Filed: Sep. 8, 2016

(65) Prior Publication Data

US 2016/0374707 A1   Dec. 29, 2016

Related U.S. Application Data

(63) Continuation of application No. PCT/JP2015/068336, filed on Jun. 25, 2015.

(30) Foreign Application Priority Data

Jul. 2, 2014   (JP) .................................. 2014-136975

(51) Int. Cl.
   *A61B 17/32*   (2006.01)
   *A61N 7/00*   (2006.01)
(52) U.S. Cl.
   CPC ........ *A61B 17/320068* (2013.01); *A61N 7/00* (2013.01); *A61B 2017/320072* (2013.01)
(58) Field of Classification Search
   CPC ........... A61B 17/320068; A61B 2017/320072; A61N 7/00
   See application file for complete search history.

(56) References Cited

U.S. PATENT DOCUMENTS 5,527,273 A * 6/1996 Manna ............. A61B 17/22012
                                                              604/22
D558,347 S * 12/2007 Darnold ....................... D24/152
(Continued)

FOREIGN PATENT DOCUMENTS

JP   H10-507378 A   7/1998
JP   2010-000336 A   1/2010
(Continued)

OTHER PUBLICATIONS

Jan. 17, 2017 International Preliminary Report on Patentability issued in PCT/JP2015/068336.
(Continued)

*Primary Examiner* — Todd J Scherbel
*Assistant Examiner* — Son Dang
(74) *Attorney, Agent, or Firm* — Oliff PLC

(57) ABSTRACT

In a width dimension decrease portion forming a distal end of an ultrasonic probe, a width dimension decreases from a proximal direction toward a distal direction, so that a sectional area perpendicular to a longitudinal axis decreases from the proximal direction toward the distal direction. An intermediary portion continuous between a probe body portion and the width dimension decrease portion includes a width dimension increase portion in which the width dimension increases and a thickness dimension decreases from the proximal direction toward the distal direction at the same time. In the intermediary portion, the sectional area perpendicular to the longitudinal axis does not increase and does not decrease at a higher decrease rate than in the width dimension decrease portion toward the distal direction.

9 Claims, 7 Drawing Sheets

(56) References Cited

U.S. PATENT DOCUMENTS

| | | | |
|---|---|---|---|
| D620,595 S * | 7/2010 | Pinel .......................... D24/144 |
| 2004/0102804 A1* | 5/2004 | Chin ................ A61B 17/00008 | 606/190 |
| 2009/0318944 A1* | 12/2009 | Kimura .................. A61B 17/16 | 606/169 |
| 2010/0057118 A1* | 3/2010 | Dietz ............. A61B 17/320068 | 606/169 |
| 2010/0168741 A1* | 7/2010 | Sanai ............ A61B 17/320068 | 606/42 |

FOREIGN PATENT DOCUMENTS

| | | | |
|---|---|---|---|
| JP | 2010-522034 A | 7/2010 |
| JP | 2012-501735 A | 1/2012 |
| WO | 2010/076873 A1 | 7/2010 |

OTHER PUBLICATIONS

Sep. 29, 2015 International Search Report issued in Patent Application No. PCT/JP2015/068336.

* cited by examiner

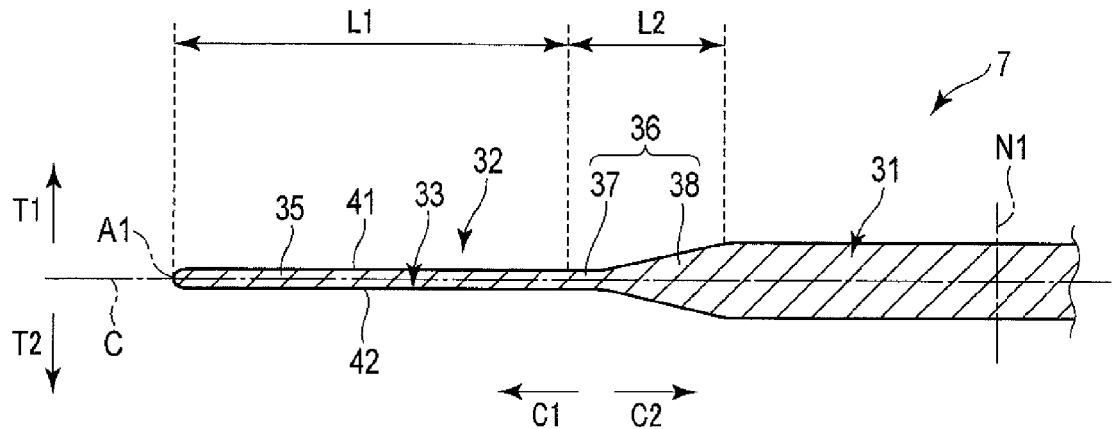
F I G. 4
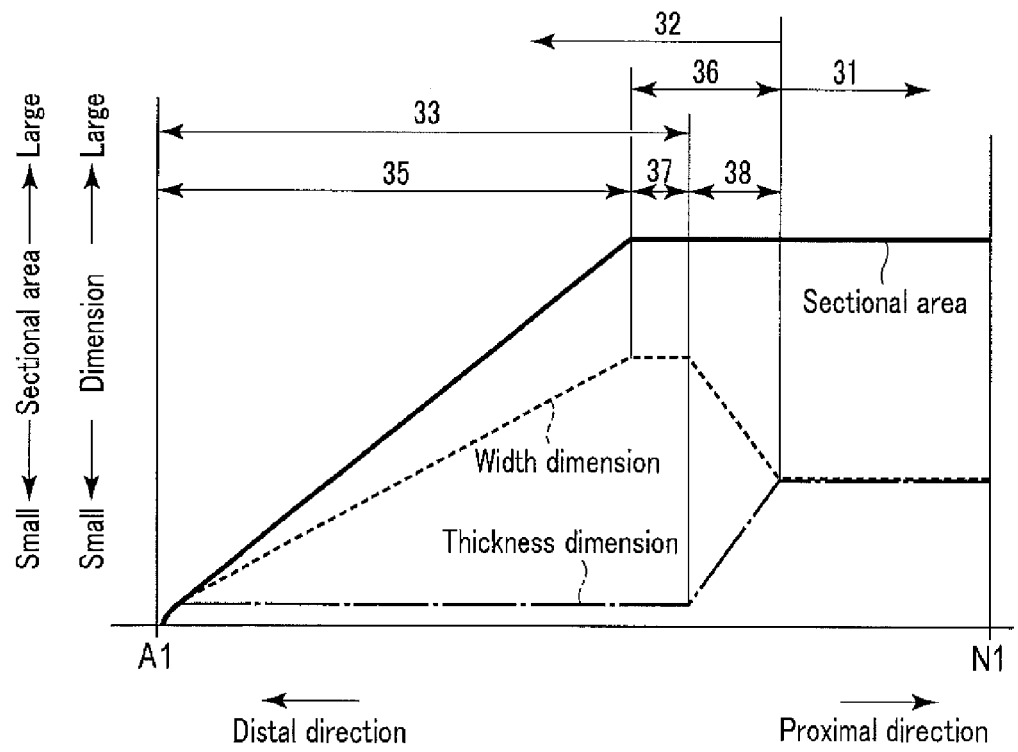
F I G. 5

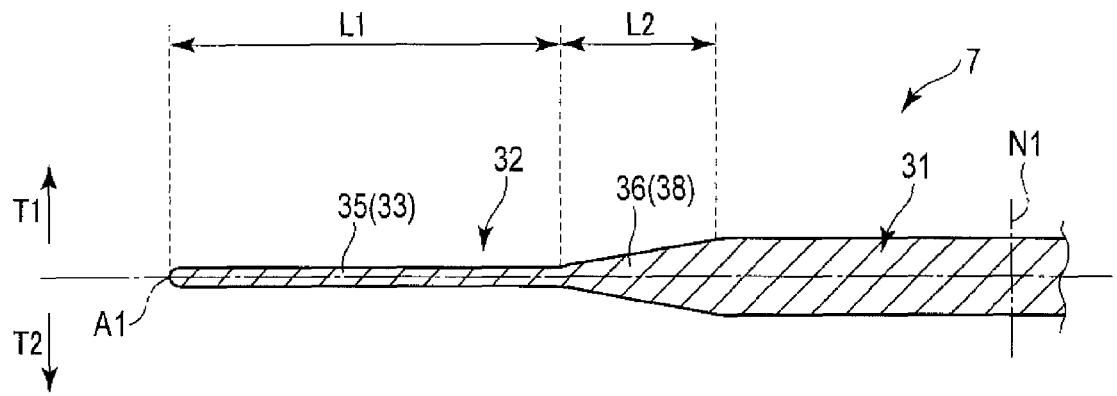
F I G. 14
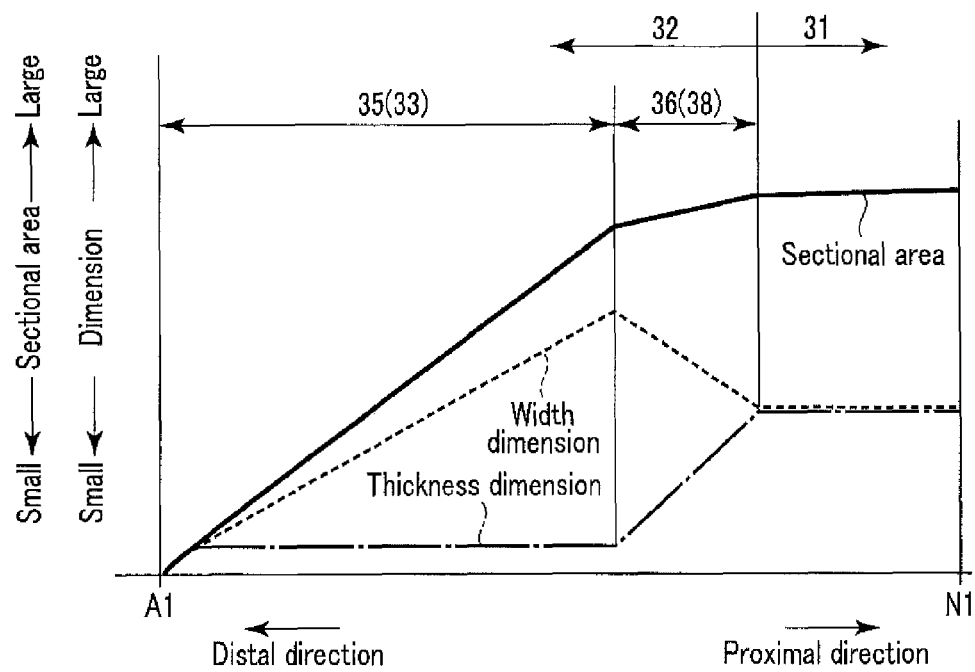
F I G. 15

ULTRASONIC PROBE AND ULTRASONIC TREATMENT INSTRUMENT

CROSS-REFERENCE TO RELATED APPLICATIONS

This is a Continuation Application of PCT Application No. PCT/JP2015/068336, filed Jun. 25, 2015 and based upon and claiming the benefit of priority from prior Japanese Patent Application No. 2014-136975, filed Jul. 2, 2014, the entire contents of which are incorporated herein by reference.

BACKGROUND OF THE INVENTION

1. Field of the Invention

The present invention relates to an ultrasonic probe capable of transmitting an ultrasonic vibration from a proximal direction toward a distal direction, and an ultrasonic treatment instrument including the ultrasonic probe.

2. Description of the Related Art

Jpn. PCT National Publication No. 2010-522034 discloses an ultrasonic treatment instrument including an ultrasonic probe capable of transmitting an ultrasonic vibration from a proximal direction toward a distal direction. A probe body portion extending along a longitudinal direction is provided in the ultrasonic probe. A distal treatment portion configured to treat a treated target such a living tissue by use of the transmitted ultrasonic vibration is provided in a distal portion of the ultrasonic probe. A plate-shaped portion (blade portion) is provided in the distal treatment portion. The distal end of the ultrasonic probe is formed by the plate-shaped portion. Certain two directions perpendicular to (intersect with) the longitudinal direction and opposite to each other are width directions, and two directions perpendicular to the longitudinal direction and perpendicular to the width directions are thickness directions. In the plate-shaped portion, a width dimension in the width directions is larger than a thickness dimension in the thickness directions. In the plate-shaped portion, an edge surface which is formed from a side edge facing in the width directions and a distal edge facing in the distal direction are provided, and a blade portion is provided in the edge surface. A sectional area decrease portion is continuous between the probe body portion and the plate-shaped portion in the longitudinal direction parallel to a longitudinal axis. In the sectional area decrease portion, the thickness dimension in the thickness directions decreases from the proximal direction toward the distal direction, and a sectional area perpendicular to the longitudinal axis decreases from the proximal direction toward the distal direction. In a state where the ultrasonic probe (treatment portion) vibrates in response to the ultrasonic vibration, the blade portion of the plate-shaped portion is brought into contact with the treated target, and the treated target is thereby cut open. In a state where the ultrasonic vibration is transmitted, the ultrasonic probe performs a longitudinal vibration whose vibration direction is parallel to the longitudinal axis.

BRIEF SUMMARY OF THE INVENTION

According to one aspect of the invention, an ultrasonic probe having a longitudinal axis, including: a probe body portion which extends along the longitudinal axis, and which is configured to transmit an ultrasonic vibration from a proximal direction toward a distal direction; a width dimension decrease portion which is provided on a distal direction side with respect to the probe body portion, and which forms a distal end of the ultrasonic probe, when certain two directions perpendicular to the longitudinal axis and opposite to each other are width directions and when two directions perpendicular to the longitudinal axis and perpendicular to the width directions are thickness directions, a width dimension in the width directions being larger than a thickness dimension in the thickness directions at a proximal end of the width dimension decrease portion, and the width dimension decreasing from the proximal direction toward the distal direction so that a sectional area perpendicular to the longitudinal axis decreases from the proximal direction toward the distal direction; a width dimension increase portion in which the width dimension in the width directions increases and the thickness dimension in the thickness directions decreases at the same time from the proximal direction toward the distal direction; and an intermediary portion in which the width dimension increase portion is provided, and which is continuous between the probe body portion and the width dimension decrease portion in longitudinal directions parallel to the longitudinal axis, the sectional area perpendicular to the longitudinal axis being kept uniform in a given range or decreasing from the proximal direction toward the distal direction in the intermediary portion, and decreasing at a lower decrease rate from the proximal direction toward the distal direction in the intermediary portion than in the width dimension decrease portion.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4 is a sectional view schematically showing the configuration of the distal portion of the ultrasonic probe in a section perpendicular to width directions according to the first embodiment;

FIG. 5 is a schematic diagram showing the change of a width dimension in the width directions, the change of a thickness dimension in the thickness directions, and the change of a sectional area perpendicular to a longitudinal axis versus the positional change in longitudinal directions in the distal portion of the ultrasonic probe according to the first embodiment;

FIG. 14 is a sectional view schematically showing the configuration of the distal portion of the ultrasonic probe in a section perpendicular to the width directions according to the second modification; and FIG. 15 is a schematic diagram showing the change of the width dimension in the width directions, the change of the thickness dimension in the thickness directions, and the change of the sectional area perpendicular to the longitudinal axis versus the positional change in longitudinal directions in the distal portion of the ultrasonic probe according to the second modification.

DETAILED DESCRIPTION OF THE INVENTION

First Embodiment

A first embodiment of the present invention is described with reference to FIG. 1 to FIG. 10.

Figure 1:
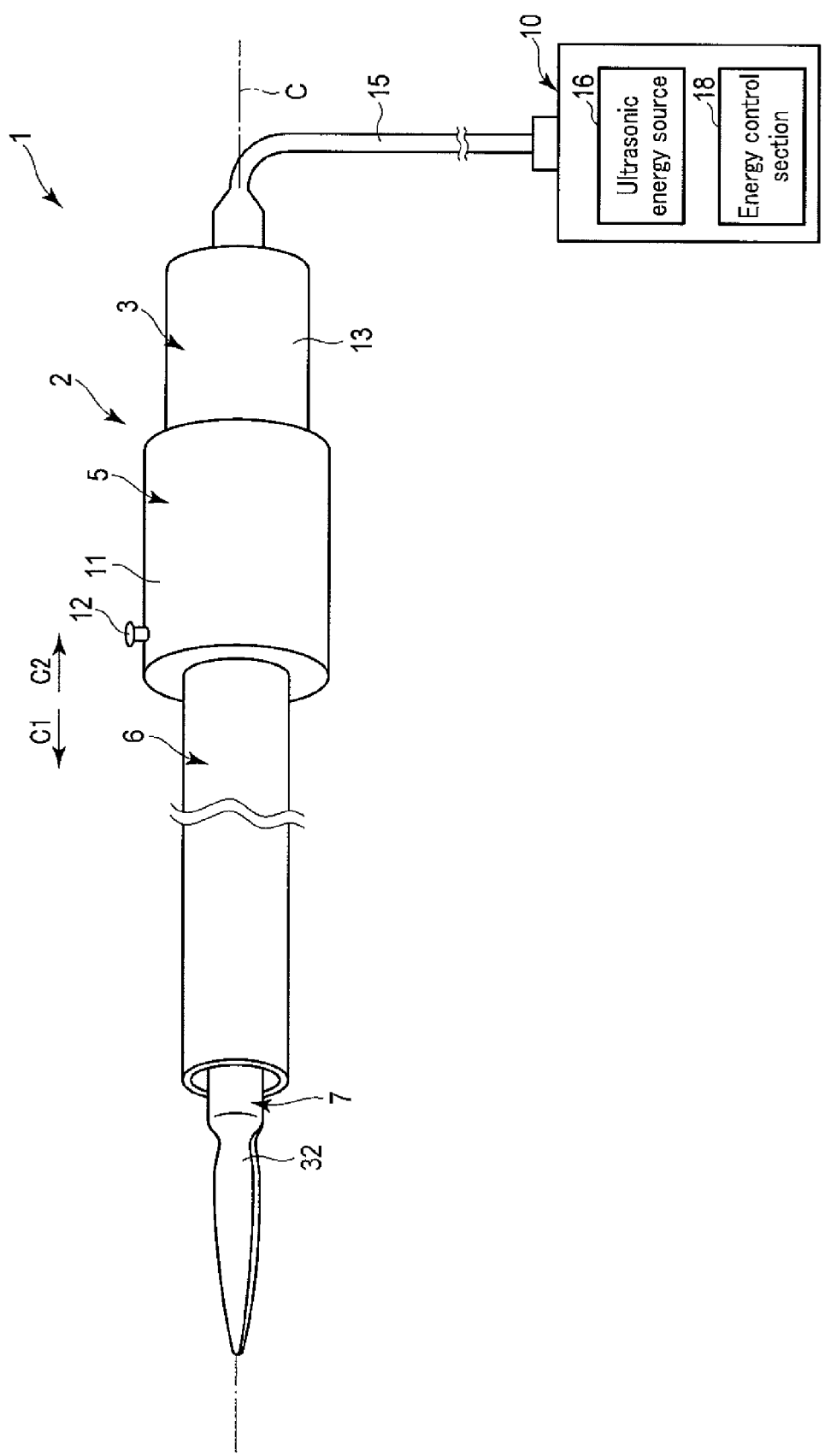
FIG. 1 is a schematic diagram showing an ultrasonic treatment system according to a first embodiment.

FIG. 1 is a diagram showing an ultrasonic treatment system (ultrasonic treatment apparatus) 1 according to the present embodiment. As shown in FIG. 1, the ultrasonic treatment system 1 includes an ultrasonic treatment instrument 2. The ultrasonic treatment instrument 2 has a straight longitudinal axis C. One of directions parallel to a longitudinal axis C is a distal direction (direction of an arrow C1 in FIG. 1), and the direction opposite to the distal direction is a proximal direction (direction of an arrow C2 in FIG. 1). Two directions (the distal direction and the proximal direction) parallel to the longitudinal axis C (along the longitudinal axis C) are longitudinal directions.

The ultrasonic treatment instrument 2 includes a transducer unit 3, a holding unit 5, a sheath 6, and an ultrasonic probe 7. The holding unit 5 includes a cylindrical case portion 11 extending along the longitudinal axis C. An energy operation input button 12 which is an energy operation input portion is attached to the cylindrical case portion 11.

The transducer unit 3 includes a transducer case 13. When the vibrator case 13 is inserted into the cylindrical case portion 11 from the proximal direction side, the transducer unit 3 is coupled to the holding unit 5. One end of a cable 15 is connected to a proximal portion of the oscillator case 13. The other end of the cable 15 is connected to an energy source unit 10. The energy source unit 10 includes an ultrasonic energy source (ultrasonic electric power source) 16 and an energy control section 18. The energy source unit 10 is, for example, an energy generator (electric power generator), and the ultrasonic energy source 16 is, for example, an electricity source provided in the energy generator.

The energy control section 18 is provided in, for example, the energy generator, and is formed from a processor including a central processing unit (CPU) or an application specific integrated circuit (ASIC). A switch section (not shown) is provided inside the cylindrical case portion 11. The energy control section 18 is electrically connected to the switch section via a signal path (not shown) extending through the transducer case 13 and the cable 15. If an energy operation in the energy operation input button 12 is input, the switch section is turned on, and an operation signal is transmitted to the energy control section 18 via the signal path. On the basis of the transmitted operation signal, the energy control section 18 controls the output state of an ultrasonic generating energy (ultrasonic generating electric power) from the ultrasonic energy source 16.

Figure 2:
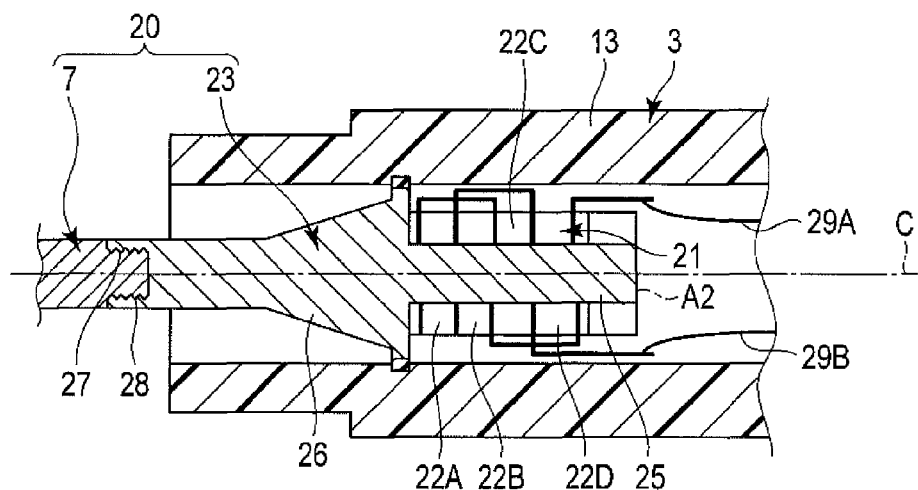
FIG. 2 is a sectional view schematically showing the configuration of a transducer unit according to the first embodiment.

FIG. 2 is a diagram showing the configuration of the transducer unit 3. As shown in FIG. 2, the transducer unit 3 includes the aforementioned transducer case 13, and an ultrasonic transducer 21 which is a vibration generator provided inside the oscillator case 13. The ultrasonic transducer 21 includes (four, in the present embodiment) piezoelectric elements 22A to 22D which convert an electric current (alternating electric current) to an ultrasonic vibration. Thus, the ultrasonic vibration is generated in the ultrasonic vibrator 21 by the transmission of ultrasonic generating energy (ultrasonic generating electric power) to the ultrasonic oscillator 21.

A horn member 23 extending along the longitudinal axis C is provided inside the transducer case 13. The horn member 23 includes a transducer attachment portion 25. Members such as the piezoelectric elements 22A to 22D that form the ultrasonic transducer 21 are attached to the vibrator attachment portion 25. A sectional area changing portion 26 is formed in the horn member 23. In the sectional area changing portion 26, the sectional area perpendicular to the longitudinal axis C decreases toward the distal direction. The amplitude of ultrasonic vibration is increased by the sectional area changing portion 26. An internal thread 27 is provided in the distal portion of the horn member 23.

As shown in FIG. 2, an external thread 28 is provided in the proximal portion of the ultrasonic probe 7. When the external thread 28 is screwed into the internal thread 27, the ultrasonic probe 7 is connected to the distal direction side of the horn member 23. The ultrasonic probe 7 extends along the longitudinal axis C. The horn member 23 is connected to the ultrasonic probe 7 inside the cylindrical case portion 11.

The ultrasonic transducer 21 which is a vibration generator is located on the proximal direction side with respect to the ultrasonic probe 7.

As shown in FIG. 1, the sheath 6 is inserted into the cylindrical case portion 11 from the distal direction side, and thereby coupled to the holding unit 5. The sheath 6 is then coupled to the transducer case 13 inside the cylindrical case portion 11. The ultrasonic probe 7 is inserted through the sheath 6. Thus, the distal portion of the ultrasonic probe 7 protrudes toward the distal direction from the distal end of the sheath 6.

As shown in FIG. 2, one end of each of electric wiring lines 29A and 29B is connected to the ultrasonic oscillator 21. The electric wiring lines 29A and 29B extend through an inside of the cable 15, and the other end of each of the electric wiring lines 29A and 29B is connected to the ultrasonic energy source 16 of the energy source unit 10. When the ultrasonic generating electric power is supplied to the ultrasonic transducer 21 from the ultrasonic energy source 16 via the electric wiring lines 29A and 29B, the ultrasonic vibration is generated in the ultrasonic transducer 21. The generated ultrasonic vibration is then transmitted to the ultrasonic probe 7 from the ultrasonic vibrator 21 via the horn member 23. A vibration transmission unit 20 which transmits the ultrasonic vibration generated in the ultrasonic transducer 21 toward the distal direction from the proximal direction is formed by the horn member 23 and the ultrasonic probe 7.

The vibration transmission unit 20 vibrates in a prescribed vibration mode (vibration state) for use in a treatment by transmitting the ultrasonic vibration generated in the ultrasonic transducer 21. In the prescribed vibration mode, the vibration transmission unit 20 performs a longitudinal vibration whose vibration direction is parallel to the longitudinal axis C (longitudinal directions). In the prescribed vibration mode, the distal end of the vibration transmission unit 20 (the distal end of the ultrasonic probe 7) and the proximal end of the vibration transmission unit 20 (the proximal end of the horn member 23) are antinode positions of the longitudinal vibration. Here, an antinode position (most-distal antinode position) A1 located at the distal end of the vibration transmission unit 20 is located most distally among the antinode positions of the longitudinal vibration, and an antinode position (most-proximal antinode position) A2 located at the proximal end of the vibration transmission unit 20 is located most proximally among the antinode positions of the longitudinal vibration. In the prescribed vibration mode, the number of antinode positions of the longitudinal vibration and the number of node positions of the longitudinal vibration between the distal end of the vibration transmission unit 20 and the proximal end of the vibration transmission unit 20 are fixed, and at least one node position of the longitudinal vibration is present between the distal end of the vibration transmission unit 20 and the proximal end of the vibration transmission unit 20. The energy control section 18 adjusts the resonant frequency of the vibration transmission unit 20 by adjusting the frequency of the electric current (alternating electric current) supplied to the ultrasonic transducer 21, and longitudinally vibrates the vibration transmission unit 20 in the prescribed vibration mode. The prescribed vibration mode (i.e. the numbers of node positions and antinode positions of the longitudinal vibration) is determined in accordance with, for example, the dimensions of the vibration transmission unit 20 to be used in the longitudinal directions, and the resonant frequency of the longitudinal vibration to be used in a treatment.

Figure 3:
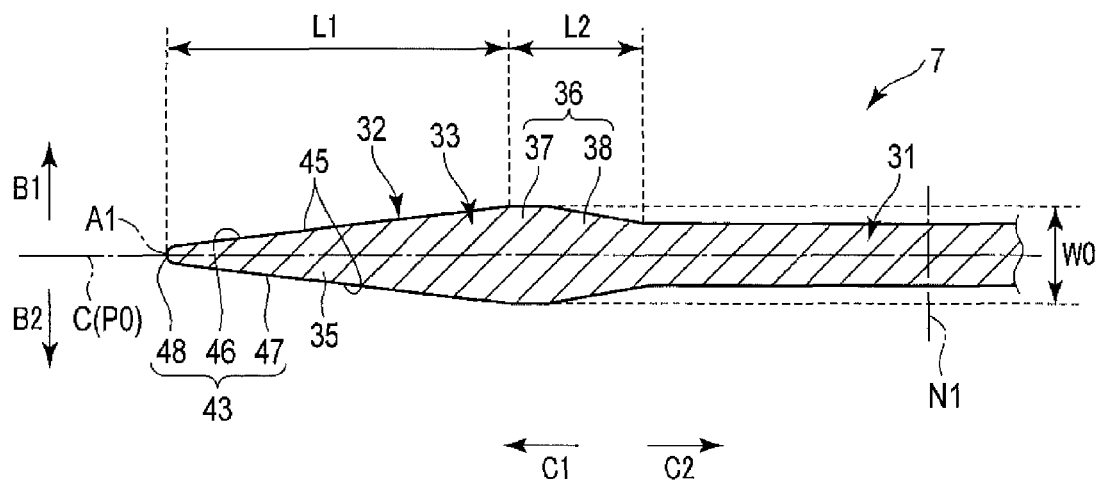
FIG. 3 is a sectional view schematically showing the configuration of a distal portion of an ultrasonic probe in a section perpendicular to thickness directions according to the first embodiment.

FIG. 3 and FIG. 4 are diagrams showing the distal portion of the ultrasonic probe 7. Here, certain two directions perpendicular to (intersect with) the longitudinal axis C and opposite to each other are width directions. One of the width directions is a first width direction (direction of an arrow B1 in FIG. 3) which is a first perpendicular direction, and the direction opposite to the first width direction is a second width direction (direction of an arrow B2 in FIG. 3) which is a second perpendicular direction. Two directions perpendicular to the longitudinal axis C and perpendicular to the width directions are thickness directions. One of the thickness directions is a first thickness direction (direction of an arrow T1 in FIG. 4) which is a third perpendicular direction, and the direction opposite to the first thickness direction is a second thickness direction (direction of an arrow T2 in FIG. 4) which is a fourth perpendicular direction. A section perpendicular to the thickness directions is shown in FIG. 3, and a section perpendicular to the width directions is shown in FIG. 4.

As shown in FIG. 3 and FIG. 4, the ultrasonic probe 7 includes a probe body portion 31 extending along the longitudinal axis C. The ultrasonic vibration transmitted to the ultrasonic probe 7 is transmitted toward the distal direction from the proximal direction in the probe body portion 31. The longitudinal axis C of the ultrasonic treatment instrument 2 serves as the central axis of the ultrasonic probe 7 including the probe body portion 31. Therefore, the ultrasonic probe 7 has the longitudinal axis C which serves as the central axis of the probe body portion 31. In the ultrasonic probe 7, a distal treatment portion 32 is provided on the distal direction side with respect to the probe body portion 31. The distal treatment portion 32 treats a treated target such as a living tissue by use of the ultrasonic vibration transmitted through the probe body portion 31. The distal end of the ultrasonic probe 7 (the vibration transmission unit 20) is formed by the distal treatment portion 32. The ultrasonic probe 7 is inserted through the sheath 6 in a state where the distal treatment portion 32 protrudes toward the distal direction from the distal end of the sheath 6.

As described above, in the prescribed vibration mode, the antinode position A1 of the longitudinal vibration is located at the distal end. A node position (most-distal node position) N1 located most distally among the node positions of the longitudinal vibration in the prescribed vibration mode is defined. In the prescribed vibration mode, the node position N1 is located on the proximal direction side with respect to the distal treatment portion 32, and located in the probe body portion 31. Therefore, the node position N1 of the longitudinal vibration is located inside the sheath 6. A plate-shaped portion (blade portion) 33 is provided in the distal treatment portion 32 located on the distal direction side with respect to the probe body portion 31. FIG. 5 is a diagram showing the change of a width dimension in the width directions, the change of a thickness dimension in the thickness directions, and the change of a sectional area perpendicular to the longitudinal axis versus the positional change in the longitudinal directions in the distal portion of the ultrasonic probe 7. In FIG. 5, the change of the sectional area along the longitudinal axis C in the distal treatment portion 32 which is continuous on the distal direction side of the probe body portion 31 and the distal portion of the probe body portion 31 is indicated by a solid line, the change of the width dimension is indicated by a broken line, and the change of the thickness dimension is indicated by an alternate long and short dashed line.

As shown in FIG. 3 to FIG. 5, the plate-shaped portion 33 includes a width dimension decrease portion 35 in which the width dimension that is a dimension in the width directions decreases from a proximal direction (direction of an arrow C2 in FIG. 3 and FIG. 4) toward a distal direction (direction of an arrow C1 in FIG. 3 and FIG. 4). By decreasing in the width dimension from the proximal direction toward the distal direction, the sectional area perpendicular to the longitudinal axis C decreases from the proximal direction toward the distal direction in the width dimension decrease portion 35. The distal end of the ultrasonic probe 7 is formed by the width dimension decrease portion 35.

At the proximal end of the width dimension decrease portion 35, the width dimension in the width directions of the ultrasonic probe 7 (the width dimension decrease portion 35) is larger than the thickness dimension that is a dimension in the thickness directions of the ultrasonic probe 7 (the width dimension decrease portion 35). At the proximal end of the width dimension decrease portion 35, the width dimension of the ultrasonic probe 7 is the maximum, so that the width dimension at the proximal end of the width dimension decrease portion 35 is a maximum width dimension W0. In the present embodiment, the thickness dimension is kept uniform (substantially uniform) over the entire length of the width dimension decrease portion 35 in the longitudinal directions. The case where the dimension is uniform includes not only the case where the dimension is the same over the entire length in the longitudinal directions but also includes the case where the dimension can be regarded as the same over the entire length in the longitudinal directions because the dimension changes along the longitudinal directions due to errors in design and manufacture but the change amount is small. For example, if a change amount is in a range of ±0.1 mm which has no particular problem as ultrasonic characteristics, the dimension is regarded as the same over the entire length in the longitudinal directions.

In the distal treatment portion 32, an intermediary portion 36 is continuous on the proximal direction side of the width dimension decrease portion 35. The intermediary portion 36 is continuous between the probe body portion 31 and the width dimension decrease portion 35 in the longitudinal directions parallel to the longitudinal axis C. The intermediary portion 36 includes a dimensionally uniform portion 37 which is continuous on the proximal direction side of the width dimension decrease portion 35, and a width dimension increase portion 38 which is continuous between the probe body portion 31 and the dimensionally uniform portion 37 in the longitudinal directions. The dimensionally uniform portion 37 forms a part of the plate-shaped portion 33. In the dimensionally uniform portion 37, the width dimension in the width directions and the thickness dimension in the thickness directions of the ultrasonic probe 7 do not change from the proximal direction toward the distal direction, and the width dimension and the thickness dimension are kept uniform (substantially uniform) over the entire length of the dimensionally uniform portion 37 in the longitudinal directions. Thus, in the dimensionally uniform portion 37, the sectional area perpendicular to the longitudinal axis C is uniform over the entire length in the longitudinal directions.

The case where the sectional area is uniform includes not only the case where the sectional area is the same over the entire length in the longitudinal directions but also includes the case where the sectional area can be regarded as the same over the entire length in the longitudinal directions because the sectional area changes along the longitudinal directions due to errors in design and manufacture but the change amount is small. For example, if a change amount is in a range of ±0.1 mm which has no particular problem as ultrasonic characteristics, the sectional area is regarded as the same over the entire length in the longitudinal directions.

The width dimension of the ultrasonic probe 7 in the dimensionally uniform portion 37 corresponds to the maximum width dimension W0 which is the width dimension at the proximal end of the width dimension decrease portion 35. The thickness dimension of the ultrasonic probe 7 in the dimensionally uniform portion 37 corresponds to the thickness dimension of the width dimension decrease portion 35. Thus, in the dimensionally uniform portion 37, the width dimension in the width directions is larger than the thickness dimension in the thickness directions. In the plate-shaped portion (blade portion) 33 formed from the dimensionally uniform portion 37 and the width dimension decrease portion 35, the thickness dimension in the thickness directions is kept uniform (substantially uniform), and the thickness dimension in the thickness directions is small. A reference plane P0 which passes through the longitudinal axis C (the central axis of the ultrasonic probe 7) and which is perpendicular to the width directions is defined. The plate-shaped portion 33 including the width dimension decrease portion 35 is plane-symmetrical with respect to the reference plane P0 as a central plane (relative to the reference plane P0) over the entire length in the longitudinal directions.

In the width dimension increase portion 38, the width dimension in the width directions increases from the proximal direction toward the distal direction. In the width dimension increase portion 38, the thickness dimension in the thickness directions decreases from the proximal direction toward the distal direction. The thickness dimension in the thickness directions at the distal end of the width dimension increase portion 38 corresponds to the thickness dimension in the plate-shaped portion 33 (the width dimension decrease portion 35 and the dimensionally uniform portion 37). The width dimension in the width directions at the distal end of the width dimension increase portion 38 corresponds to the maximum width dimension W0 which is the width dimension at the proximal end of the width dimension decrease portion 35. Therefore, in the width dimension increase portion 38, the width dimension increases up to the maximum width dimension W0 from the proximal direction toward the distal direction. However, in the width dimension increase portion 38, the width dimension and the thickness dimension change along the longitudinal directions as described above, but the sectional area perpendicular to the longitudinal axis C is uniform over the entire length in the longitudinal directions. That is, in the width dimension increase portion 38, the width dimension and the thickness dimension change so that the sectional area perpendicular to the longitudinal axis C is uniform over the entire length in the longitudinal directions.

Since the dimensionally uniform portion 37 and the width dimension increase portion 38 have the configurations described above, the width dimension in the width directions increases or is kept uniform in a given range and does not decrease from the proximal direction toward the distal direction in the intermediary portion 36 formed from the dimensionally uniform portion 37 and the width dimension increase portion 38. In the intermediary portion 36 according to the present embodiment, the sectional area perpendicular to the longitudinal axis C is uniform over the entire length in the longitudinal directions. Therefore, in the intermediary portion 36, the sectional area perpendicular to the longitudinal axis C is kept uniform in a given range from the proximal direction toward the distal direction, that is, does not increase from the proximal direction to the distal direction and does not decrease from the proximal direction to the distal direction. Thus, in the part located on the proximal direction side of the width dimension decrease portion 35, the thickness dimension in the thickness directions decreases, but the sectional area perpendicular to the longitudinal axis C does not decrease.

A dimension of the width dimension decrease portion 35 in the longitudinal directions is a first longitudinal dimension L1, and a dimension of the intermediary portion 36 in the longitudinal directions is a second longitudinal dimension L2. The first longitudinal dimension L1 is larger than the second longitudinal dimension L2. The first longitudinal dimension L1 of the width dimension decrease portion 35 increases so that the width dimension in the width directions decreases at a low decrease rate (gently) from the proximal direction toward the distal direction in the width dimension decrease portion 35. Therefore, in the width dimension decrease portion 35, the sectional area perpendicular to the longitudinal axis C decreases at a low decrease rate (gently) from the proximal direction toward the distal direction, and does not decrease sharply (at a high decrease rate) from the proximal direction to the distal direction.

In the prescribed vibration mode, the node position (most-distal node position) N1 is located in the probe body portion 31, and the node position N1 is therefore located on the proximal direction side with respect to the proximal end of the intermediary portion 36. As described above, in the width dimension decrease portion 35 and the intermediary portion 36, the sectional area perpendicular to the longitudinal axis C is kept uniform in a given range or decreases and does not increase from the proximal direction toward the distal direction. In the probe body portion 31, the width dimension, the thickness dimension, and the sectional area perpendicular to the longitudinal axis C do not change along the longitudinal directions in a part located on the distal direction side with respect the node position N1. Thus, between the node position (mos-distal node position) N1 and the antinode position (most-distal antinode position) A1 in the longitudinal directions, the sectional area perpendicular to the longitudinal axis C of the ultrasonic probe 7 is uniformly kept in a constant size or decreases and does not increase from the proximal direction toward the distal direction. Since the sectional area perpendicular to the longitudinal axis C does not increase from the proximal direction toward the distal direction, the amplitude of the longitudinal vibration does not decrease in a part located on the distal direction side with respect to the node position N1.

The width dimension decrease portion 35 includes a first outer surface 41 facing in the first thickness direction, and a second outer surface 42 facing in the second thickness direction. In the width dimension decrease portion 35, an edge surface 43 is continuous between the first outer surface 41 and the second outer surface 42. A blade portion (blade) 45 is formed in at least part of the edge surface 43. The edge surface 43 includes a first side edge 46 facing in the first width direction, a second side edge 47 facing in the second width direction, and a distal edge 48 facing in the distal direction. The distal end of the ultrasonic probe 7 is formed by the distal edge 48.

Next, functions and advantageous effects of the ultrasonic probe 7 and the ultrasonic treatment instrument 2 according to the present embodiment are described. When the ultrasonic treatment system 1 is used to treat a treated target such as a living tissue (blood vessel), the ultrasonic probe 7 and the sheath 6 are inserted into a body cavity. An energy operation is then input in the energy operation input button 12. Accordingly, an ultrasonic generating energy (ultrasonic generating electric power) is output from the ultrasonic energy source 16 by the energy control section 18.

The ultrasonic generating energy (alternating electric current) is supplied to the ultrasonic transducer 21, and an ultrasonic vibration is thereby generated in the ultrasonic transducer 21. The generated ultrasonic vibration is then transmitted to the ultrasonic probe 7 via the horn member 23. In the ultrasonic probe 7 (the probe body portion 31), the ultrasonic vibration is then transmitted to the distal treatment portion 32 from the proximal direction toward the distal direction, and the vibration transmission unit 20 including the ultrasonic probe 7 longitudinally vibrates. In a state where the distal treatment portion 32 performs the longitudinal vibration whose vibration direction is parallel to the longitudinal axis C, the blade portion 45 provided in the edge surface 43 of the width dimension decrease portion 35 is brought into contact with the treated target, and the treated target is thereby cut open.

In the treatment, a high-frequency electric power (a high-frequency electric current) may be supplied to the distal treatment portion 32 simultaneously with the ultrasonic vibration. In this case, an energy source (e.g. an electricity source) separate from the ultrasonic energy source 16 is provided in, for example, the energy source unit 10, and the high-frequency electric power (high-frequency energy) is output from the energy source. The output high-frequency electric power is then supplied to the distal treatment portion 32 through electric wiring lines (not shown) different from the electric wiring lines 29A and 29B extending through the inside of the cable 15, the horn member 23, and the ultrasonic probe 7. Moreover, high-frequency electric power is supplied to a return electrode (not shown) disposed outside the body from the energy source. Accordingly, the high-frequency electric current flows between the plate-shaped portion 33 and the return electrode outside the body, and the high-frequency electric current flows through the treated target which is in contact with the blade portion 45 of the width dimension decrease portion 35. Consequently, the treated target is cut open (cut) and coagulated (sealed) at the same time.

Figure 6:
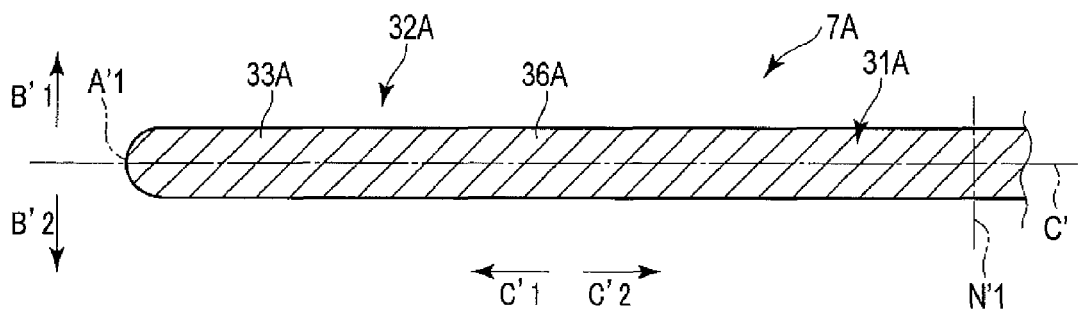
FIG. 6 is a sectional view schematically showing the configuration of a distal portion of an ultrasonic probe in a section perpendicular to thickness directions according to a comparative example.
Figure 7:
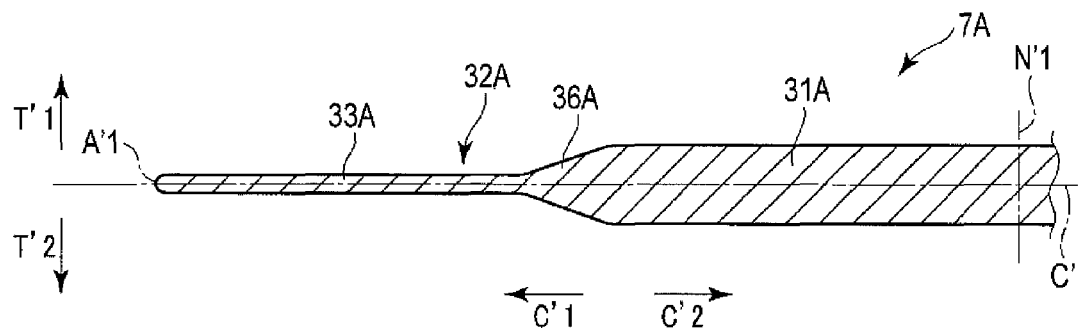
FIG. 7 is a sectional view schematically showing the configuration of the distal portion of the ultrasonic probe in a section perpendicular to width directions according to the comparative example.
Figure 8:
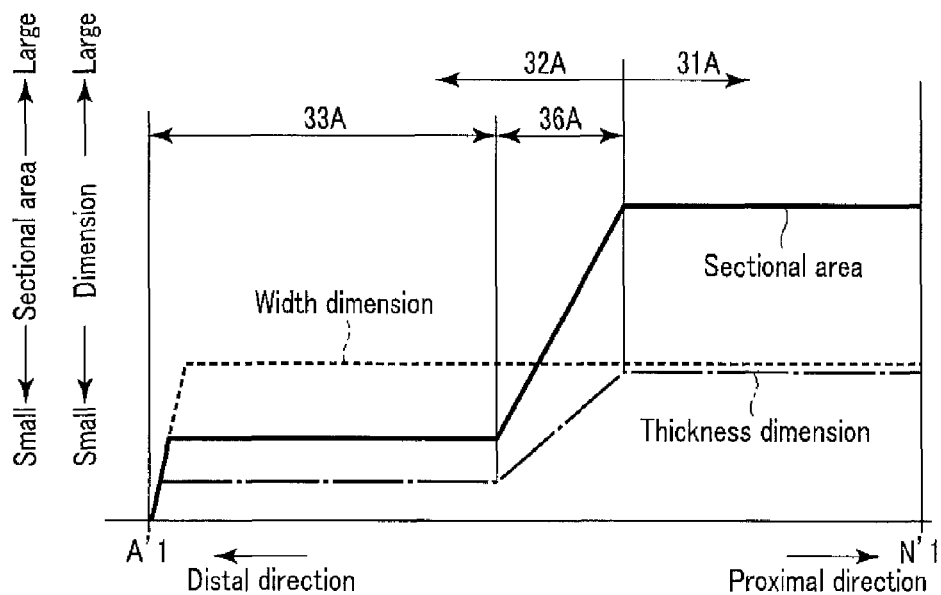
FIG. 8 is a schematic diagram showing the change of the width dimension in the width directions, the change of the thickness dimension in the thickness directions, and the change of the sectional area perpendicular to the longitudinal axis versus the positional change in longitudinal directions in the distal portion of the ultrasonic probe according to the comparative example.

Here, an ultrasonic probe 7A according to a comparative example of the present embodiment is shown in FIG. 6 and FIG. 7. FIG. 6 shows a section perpendicular to thickness directions (directions of an arrow T'1 and an arrow T'2 in FIG. 7), and FIG. 7 shows a section perpendicular to width directions (directions of an arrow B'1 and an arrow B'2 in FIG. 6). FIG. 8 is a diagram showing the change of the width dimension in the width directions, the change of the thickness dimension in the thickness directions, and the change of the sectional area perpendicular to a longitudinal axis C' versus the positional change in longitudinal directions (directions of an arrow C'1 and an arrow C'2 in FIG. 6 and FIG. 7) in the distal portion of the ultrasonic probe 7A. In FIG. 8, the change of the sectional area is indicated by a solid line, the change of the width dimension is indicated by a broken line, and the change of the thickness dimension is indicated by an alternate long and short dashed line.

In the ultrasonic probe 7A according to the comparative example, a plate-shaped portion (blade portion) 33A is provided in a distal treatment portion 32A, and the distal end of the ultrasonic probe 7A is formed by the plate-shaped portion 33A, as in the ultrasonic probe 7 according to the first embodiment. A node position N'1 located most distally among the node positions of the longitudinal vibration is located in a probe body portion 31A. However, in the comparative example, a sectional area decrease portion 36A is continuous between the probe body portion 31A and the plate-shaped portion 33A in the longitudinal directions, in contrast with the first embodiment. In the sectional area decrease portion 36A, the thickness dimension in the thickness directions sharply decreases from the proximal direction toward the distal direction. In the sectional area decrease portion 36A, the width dimension in the width directions does not change along the longitudinal directions, and does not increase from the proximal direction toward the distal direction. Therefore, in the sectional area decrease portion 36A, the sectional area perpendicular to the longitudinal axis C' decreases sharply (at a high decrease rate) from the proximal direction toward the distal direction.

In the plate-shaped portion 33A which is continuous on the distal direction side of the sectional area decrease portion 36A, the width dimension and the thickness dimension do not increase from the proximal direction to the distal direction, and the sectional area perpendicular to the longitudinal axis C' does not increase from the proximal direction toward the distal direction. Thus, in the plate-shaped portion 33A, over the entire length in the longitudinal directions, the thickness dimension in the thickness directions is small, and the sectional area perpendicular to the longitudinal axis C' is small. Therefore, the width dimension decrease portion 35 and the intermediary portion 36 that are provided in the plate-shaped portion 33 according to the present embodiment are not present in the plate-shaped portion 33A according to the comparative example.

Figure 9:
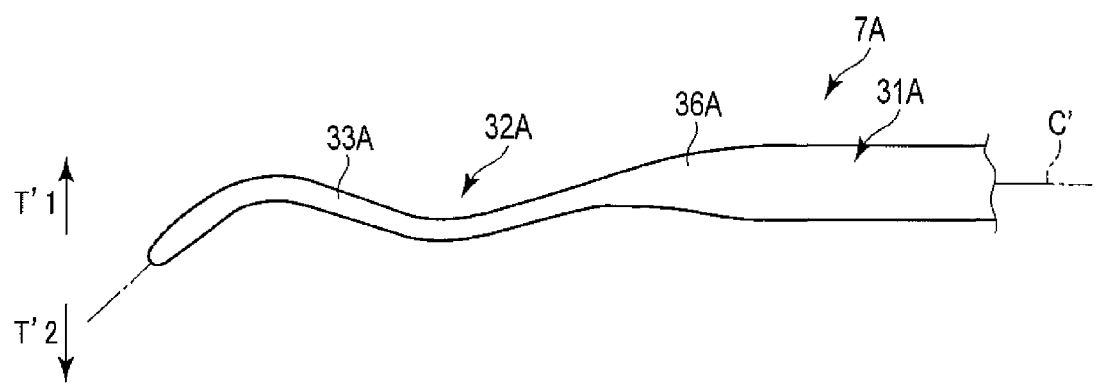
FIG. 9 is a schematic diagram illustrating a vibration state during the transmission of an ultrasonic vibration of the ultrasonic probe according to the comparative example.

FIG. 9 is a diagram illustrating a vibration state of the ultrasonic probe 7A in a state where the ultrasonic vibration is transmitted. As shown in FIG. 9, in a state where the ultrasonic probe 7A performs the longitudinal vibration whose vibration direction is parallel to the longitudinal axis in the prescribed vibration mode in response to the ultrasonic vibration, a lateral vibration whose vibration direction is parallel to the thickness directions is generated due to an external force (moment) in thickness directions (directions of an arrow T'1 and an arrow T'2 in FIG. 9) which acts on the plate-shaped portion 33A. The thickness dimension and the sectional area perpendicular to the longitudinal axis C' is small over the entire length in the longitudinal directions in the plate-shaped portion 33A, so that in a state where the ultrasonic probe 7A performs the longitudinal vibration in response to the ultrasonic vibration, the plate-shaped portion 33A is greatly subject to the external force in the thickness directions over the entire length in the longitudinal directions. Thus, in a state where the ultrasonic probe 7A performs the longitudinal vibration in response to the ultrasonic vibration, the amplitude of the lateral vibration generated in the plate-shaped portion 33A increases, and the effect of the generated lateral vibration on the longitudinal vibration increases. Because the effect of the lateral vibration on the longitudinal vibration increases in the ultrasonic probe 7A, a vibration in the ultrasonic probe 7A becomes unstable.

In contrast, in the present embodiment, the width dimension increase portion 38 which decreases in the thickness dimension and increases in the width dimension at the same time from the proximal direction toward the distal direction is provided in the intermediary portion 36 between the width dimension decrease portion 35 and the probe body portion 31 in the longitudinal directions, and the width dimension in the width directions does not decrease from the proximal direction toward the distal direction in the intermediary portion 36. In the intermediary portion 36, the sectional area perpendicular to the longitudinal axis C does not decrease from the proximal direction to the distal direction. Thus, in the part located on the proximal direction side of the width dimension decrease portion 35, the thickness dimension in the thickness directions decreases, but the sectional area perpendicular to the longitudinal axis C does not decrease. That is, in the width dimension decrease portion 35, the thickness dimension is small over the entire length in the longitudinal directions, but the sectional area perpendicular to the longitudinal axis C is small in the distal-side part alone. Moreover, in the width dimension decrease portion 35, the degree of the decrease of the sectional area perpendicular to the longitudinal axis C from the proximal direction toward the distal direction is lower than in the sectional area decrease portion 36A according to the comparative example.

Figure 10:
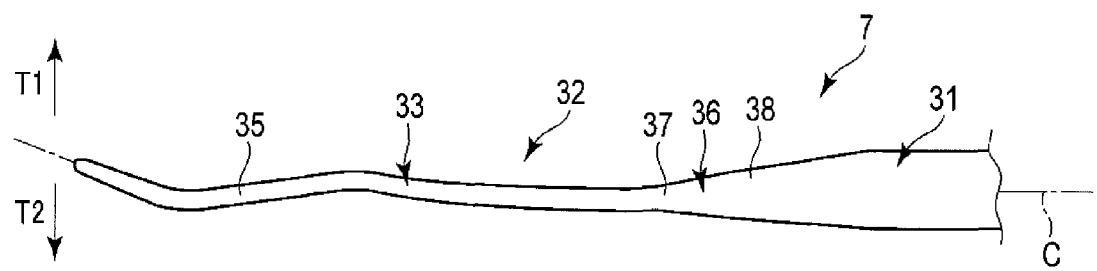
FIG. 10 is a schematic diagram illustrating a vibration state during the transmission of the ultrasonic vibration of the ultrasonic probe according to the first embodiment.

FIG. 10 is a diagram illustrating a vibration state of the ultrasonic probe 7 in a state where the ultrasonic vibration is transmitted. As described above, the sectional area perpendicular to the longitudinal axis C is not small in the proximal-side part of the width dimension decrease portion 35, and the degree of the decrease of the sectional area from the proximal direction toward the distal direction is lower in the width dimension decrease portion 35 than in the sectional area decrease portion 36A according to the comparative example. That is, if the probe body portion 31 according to the present embodiment and the probe body portion 31A according to the comparative example have the same size and shape, the proximal end of the width dimension decrease portion 35 has a larger sectional area than the proximal end of the plate-shaped portion 33A according to the comparative example, and the sectional area is larger in a range between the proximal end of the width dimension decrease portion 35 and the vicinity of the distal end thereof than in a range between the proximal end of the plate-shaped portion 33A and the vicinity of the distal end thereof according to the comparative example. Thus, as shown in FIG. 10, in a state where the ultrasonic probe 7 performs the longitudinal vibration in response to the ultrasonic vibration, the proximal-side part of the width dimension decrease portion 35 (the proximal portion of the plate-shaped portion 33) is less subject to the external force (moment) in the thickness directions. Thus, in a state where the ultrasonic probe 7 performs the longitudinal vibration in response to the ultrasonic vibration, the amplitude of the lateral vibration generated in the width dimension decrease portion 35 (the plate-shaped portion 33) does not increase, and the effect of the generated lateral vibration on the longitudinal vibration is small.

For example, in a simulation, the amplitude of lateral vibration compared to the amplitude of longitudinal vibration was about 8.5% when the ultrasonic probe 7A according to the comparative example in FIG. 6 to FIG. 9 was longitudinally vibrated in the prescribed vibration mode, whereas the amplitude of lateral vibration compared to the amplitude of longitudinal vibration was about 2% when the ultrasonic probe 7 according to the present embodiment was longitudinally vibrated in the prescribed vibration mode. In an experiment, in a state where the distal treatment portion 32A of the ultrasonic probe 7A according to the comparative example in FIG. 6 to FIG. 9 and the distal treatment portion 32 of the ultrasonic probe 7 according to the present embodiment were each longitudinally vibrating in the prescribed vibration mode, water (liquid) was dropped on their outer surfaces from one of the thickness directions, and the amount of generated mist was detected. Specifically, in a state where the distal treatment portion 32A of the ultrasonic probe 7A and the distal treatment portion 32 of the ultrasonic probe 7 were longitudinally vibrated, a predetermined amount of water (liquid) was dropped on each of the distal treatment portions 32A and 32. The water (liquid) adhering to the outer surface of each of the distal treatment portions 32A and 32 was collected, and the amount of collected water was measured. The collection amount was subtracted from the predetermined amount of the dropped water, and the amount of mist generated in each of the distal treatment portions 32A and 32 was estimated. In this case, the amplitude of the aforementioned lateral vibration was higher when the amount of generated mist was greater. In a verification by the experiment, the amount of mist generated when the ultrasonic probe 7A according to the comparative example in FIG. 6 to FIG. 9 was longitudinally vibrated in the prescribed vibration mode was twice or more than the amount of mist generated when the ultrasonic probe 7 according to the present embodiment was longitudinally vibrated in the prescribed vibration mode.

The effect of lateral vibration on the longitudinal vibration is reduced in the ultrasonic probe 7, and the stability of the vibration in the ultrasonic probe 7 is therefore ensured. This ensures the transmissibility of the ultrasonic vibration in the ultrasonic probe 7, and also ensures the strength of the ultrasonic probe 7 against the ultrasonic vibration.

In the present embodiment, in the plate-shaped portion (blade portion) 33 including the width dimension decrease portion 35, the thickness dimension in the thickness directions is small over the entire length in the longitudinal directions. This can ensure the performance of a treatment such as a treatment to cut open a treated target with blade portion 45 of the width dimension decrease portion 35.

In the present embodiment, the first longitudinal dimension L1 of the width dimension decrease portion 35 is large, and the width dimension in the width directions decreases at a low decrease rate (gently) from the proximal direction toward the distal direction in the width dimension decrease portion 35. Therefore, in the width dimension decrease portion 35, the sectional area perpendicular to the longitudinal axis C decreases at a low decrease rate (gently) from the proximal direction toward the distal direction, and does not decrease sharply (at a high decrease rate) from the proximal direction toward the distal direction. Thus, the proximal-side part of the width dimension decrease portion (the proximal portion of the plate-shaped portion 33) is less subject to the external force (moment) in the thickness directions, and the effect of lateral vibration on the longitudinal vibration can be further reduced in the ultrasonic probe 7.

Furthermore, in the ultrasonic probe 7, between the node position (most-distal node position) N1 and the antinode position (most-distal antinode position) A1 in the longitudinal directions, the sectional area perpendicular to the longitudinal axis C of the ultrasonic probe 7 does not increase from the proximal direction toward the distal direction. Since the sectional area perpendicular to the longitudinal axis C does not increase from the proximal direction toward the distal direction, the amplitude of the longitudinal vibration does not decrease in a part located on the distal direction side with respect to the node position N1. Thus, the plate-shaped portion 33 longitudinally vibrates with amplitude suited to a treatment, and the treatment performance can be improved.

(Modifications)

Figure 11:
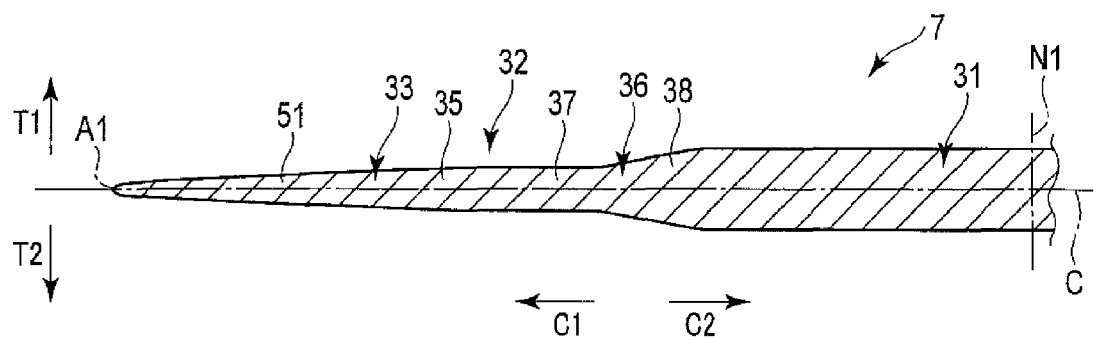
FIG. 11 is a sectional view schematically showing the configuration of the distal portion of the ultrasonic probe in a section perpendicular to the width directions according to a first modification.
Figure 12:
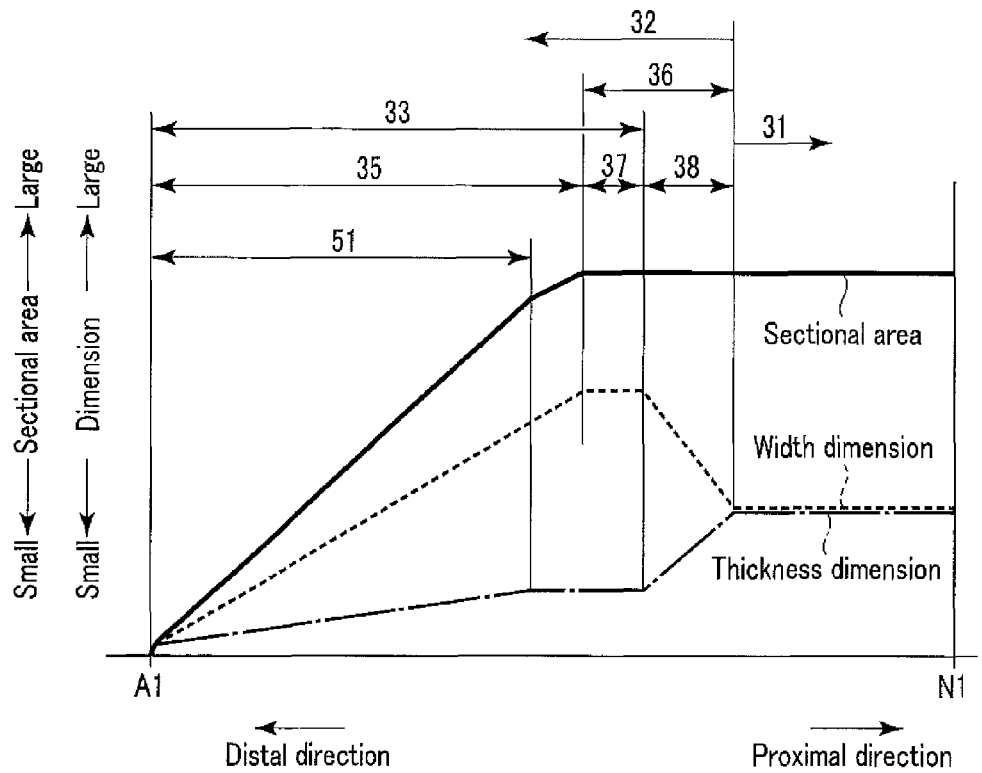
FIG. 12 is a schematic diagram showing the change of the width dimension in the width directions, the change of the thickness dimension in the thickness directions, and the change of the sectional area perpendicular to the longitudinal axis versus the positional change in the longitudinal directions in the distal portion of the ultrasonic probe according to the first modification.

Although the thickness dimension is kept uniform (substantially uniform) over the entire length in the longitudinal directions in the width dimension decrease portion 35 in the first embodiment, the present invention is not limited to this. For example, as shown in FIG. 11 and FIG. 12 according to a first modification, a thickness dimension decrease portion 51 in which the thickness dimension in thickness directions (directions of an arrow T1 and an arrow T2 in FIG. 11) of the ultrasonic probe 7 decreases from the proximal direction toward the distal direction may be provided in the width dimension decrease portion 35. FIG. 11 shows a section perpendicular to the width directions. FIG. 12 is a diagram showing the change of the width dimension in the width directions, the change of the thickness dimension in the thickness directions, and the change of the sectional area perpendicular to a longitudinal axis versus the positional change in the longitudinal directions in the distal portion of the ultrasonic probe 7. In FIG. 12, the change of the sectional area is indicated by a solid line, the change of the width dimension is indicated by a broken line, and the change of the thickness dimension is indicated by an alternate long and short dashed line.

In the thickness dimension decrease portion 51 according to the present modification, the width dimension in the width directions decreases and the thickness dimension decreases from the proximal direction toward the distal direction. In the present modification as well as in the first embodiment, the sectional area perpendicular to the longitudinal axis C decreases from the proximal direction to the distal direction in the width dimension decrease portion 35 including the thickness dimension decrease portion 51. Moreover, in the present modification as well as in the first embodiment, the sectional area perpendicular to the longitudinal axis C is uniform over the entire length of the intermediary portion 36 in the longitudinal directions.

Figure 13:
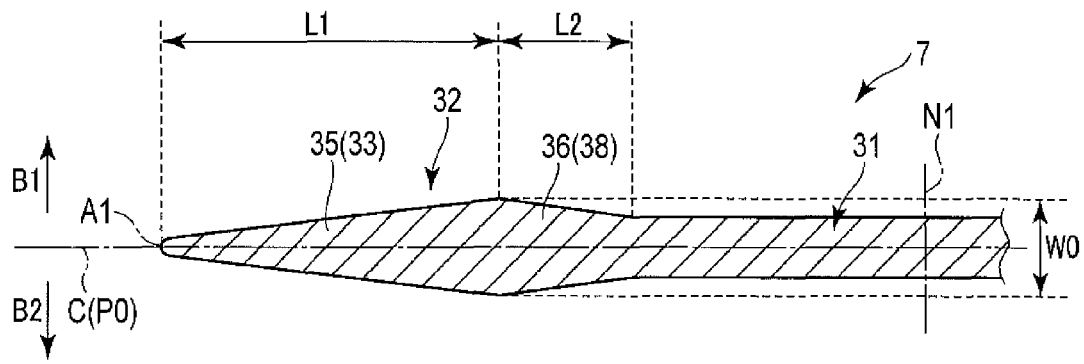
FIG. 13 is a sectional view schematically showing the configuration of the distal portion of the ultrasonic probe in a section perpendicular to the thickness directions according to a second modification.

Although the dimensionally uniform portion 37 is provided in the intermediary portion 36 in the first embodiment, it is not limited to this. For example, as shown in FIG. 13 to FIG. 15 according to a second modification, the dimensionally uniform portion (37) shown in FIG. 3 does not need to be provided. FIG. 13 shows a section perpendicular to thickness directions (directions of an arrow T1 and an arrow T2 in FIG. 14). FIG. 14 shows a section perpendicular to width directions (directions of an arrow B1 and an arrow B2 in FIG. 13). FIG. 15 is a diagram showing the change of the width dimension in the width directions, the change of the thickness dimension in the thickness directions, and the change of the sectional area perpendicular to the longitudinal axis versus the positional change in longitudinal directions (directions of an arrow C1 and an arrow C2 in FIG. 13 and FIG. 14) in the distal portion of the ultrasonic probe 7. In FIG. 15, the change of the sectional area is indicated by a solid line, the change of the width dimension is indicated by a broken line, and the change of the thickness dimension is indicated by an alternate long and short dashed line.

In the present modification, the intermediary portion 36 which is continuous between the width dimension decrease portion 35 and the probe body portion 31 in the longitudinal directions is formed from the width dimension increase portion 38 alone. Therefore, the width dimension decrease portion 35 is continuous on the distal direction side of the width dimension increase portion 38, and the probe body portion 31 is continuous on the proximal direction side of the width dimension increase portion 38. Since the intermediary portion 36 is formed from the width dimension increase portion 38 alone, the width dimension increases and the thickness dimension decreases from the proximal direction toward the distal direction over the entire length of the intermediary portion 36 in the longitudinal directions. In the present modification as well as in the first embodiment, the first longitudinal dimension L1 of the width dimension decrease portion 35 in the longitudinal directions is larger than the second longitudinal dimension L2 of the intermediary portion 36 in the longitudinal directions.

In the present modification, the decrease rate of the thickness dimension is higher than the increase rate of the width dimension in the width dimension increase portion 38 (intermediary portion 36). Thus, in the intermediary portion 36, the sectional area perpendicular to the longitudinal axis C decreases from the proximal direction toward the distal direction. However, in the intermediary portion 36, the width dimension increases from the proximal direction toward the distal direction, so that the decrease rate of the sectional area perpendicular to the longitudinal axis C in the intermediary portion 36 is lower than the decrease rate of the sectional area in the width dimension decrease portion 35. Therefore, in the intermediary portion 36, the sectional area perpendicular to the longitudinal axis C decreases at a low decrease rate (gently) from the proximal direction toward the distal direction, and does not decrease sharply. Since the second longitudinal dimension L2 of the intermediary portion 36 is small, the decrease amount of the sectional area perpendicular to the longitudinal axis C in the intermediary portion 36 is small. That is, the difference of the sectional area perpendicular to the longitudinal axis C between the proximal end of the intermediary portion 36 and the distal end of the intermediary portion 36 is small.

Since the decrease amount of the sectional area perpendicular to the longitudinal axis C in the intermediary portion 36 is small, the sectional area perpendicular to the longitudinal axis C is not small in the proximal-side part of the width dimension decrease portion 35 in the present modification as well as in the first embodiment. Thus, in a state where the ultrasonic probe 7 performs the longitudinal vibration in response to the ultrasonic vibration, the proximal-side part of the width dimension decrease portion 35 (the proximal portion of the plate-shaped portion 33) is less subject to the external force (moment) in the thickness directions. Therefore, as in the first embodiment, in a state where the ultrasonic probe 7 performs the longitudinal vibration in response to the ultrasonic vibration, the amplitude of the lateral vibration generated in the width dimension decrease portion 35 (the plate-shaped portion 33) does not increase, and the effect of the generated lateral vibration on the longitudinal vibration is reduced.

The ultrasonic probe (7) according to the embodiment and others described above (except for the comparative example) includes the probe body portion (31) which extends along the longitudinal axis (C) and which is configured to transmit an ultrasonic vibration from the proximal direction (C2) toward the distal direction (C1), and the width dimension decrease portion (35) which is provided on the distal direction (C1) side with respect to the probe body portion (31) and which forms the distal end of the ultrasonic probe (7). At the proximal end of the width dimension decrease portion (35), the width dimension in the width directions (B1 and B2) is larger than the thickness dimension in the thickness directions (T1 and T2). In the width dimension decrease portion (35), the width dimension decreases from the proximal direction (C2) toward the distal direction (C1), so that the sectional area perpendicular to the longitudinal axis (C) decreases from the proximal direction (C2) toward the distal direction (C1). The intermediary portion (36) is continuous between the probe body portion (31) and the width dimension decrease portion (35) in the longitudinal directions (C1 and C2) parallel to the longitudinal axis (C). The intermediary portion (36) includes the width dimension increase portion (38) in which the width dimension in the width directions (B1 and B2) increases and the thickness dimension in thickness directions (T1 and T2) decreases from the proximal direction (C2) toward the distal direction (C1) at the same time. In the intermediary portion (36), the sectional area perpendicular to the longitudinal axis (C) does not change along the longitudinal directions (C1 and C2) or decreases at a lower decrease rate from the proximal direction (C2) toward the distal direction (C1) than in the width dimension decrease portion (35) in any part. That is, in the intermediary portion (36), the sectional area perpendicular to the longitudinal axis (C) does not increase from the proximal direction (C2) toward the distal direction (C1), and does not decrease at a higher decrease rate from the proximal direction (C2) toward the distal direction (C1) than in the width dimension decrease portion (35).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic probe having a longitudinal axis, comprising:
    a probe body portion which extends along the longitudinal axis, and which is configured to transmit an ultrasonic vibration from a proximal direction toward a distal direction;
    a width dimension decrease portion which is provided on a distal direction side with respect to the probe body portion, and which forms a distal end of the ultrasonic probe, when certain two directions perpendicular to the longitudinal axis and opposite to each other are width directions and when two directions perpendicular to the longitudinal axis and perpendicular to the width directions are thickness directions, a width dimension in the width directions being larger than a thickness dimension in the thickness directions at a proximal end of the width dimension decrease portion, and the width dimension decreasing from the proximal direction toward the distal direction so that a sectional area perpendicular to the longitudinal axis decreases from the proximal direction toward the distal direction;
    a width dimension increase portion in which the width dimension in the width directions increases and the thickness dimension in the thickness directions decreases at the same time from the proximal direction toward the distal direction; and
    an intermediary portion in which the width dimension increase portion is provided, and which is continuous between the probe body portion and the width dimension decrease portion in longitudinal directions parallel to the longitudinal axis, the sectional area perpendicular to the longitudinal axis being kept uniform in a given range or decreasing from the proximal direction toward the distal direction in the intermediary portion, and decreasing at a lower decrease rate from the proximal direction toward the distal direction in the intermediary portion than in the width dimension decrease portion.

2. The ultrasonic probe according to claim 1, wherein in the intermediary portion, the width dimension in the width directions is kept uniform in a given range or increases from the proximal direction toward the distal direction, and
    when the width dimension in the width directions at the proximal end of the width dimension decrease portion is a maximum width dimension, the width dimension increases up to the maximum width dimension from the proximal direction toward the distal direction in the width dimension increase portion.

3. The ultrasonic probe according to claim 1, wherein the width dimension decrease portion includes a thickness dimension decrease portion in which the thickness dimension in the thickness directions decreases from the proximal direction toward the distal direction.

4. The ultrasonic probe according to claim 1, wherein the width dimension decrease portion is plane-symmetrical with respect to a reference plane passing through the longitudinal axis and perpendicular to the width directions as a central plane over the entire length in the longitudinal directions.

5. The ultrasonic probe according to claim 1, wherein in a state where the ultrasonic vibration is transmitted through the probe body portion, a most-distal antinode position located most distally among antinode positions of the longitudinal vibration is located at the distal end of the ultrasonic probe, and in the state where the ultrasonic vibration is transmitted through the probe body portion, a most-distal node position locate most distally among node positions of the longitudinal vibration is located on a proximal direction side with respect to a proximal end of the intermediary portion.

6. The ultrasonic probe according to claim 1, wherein the width dimension decrease portion includes a first outer surface facing in a first thickness direction which is one of the thickness directions, a second outer surface facing in a second thickness direction which is opposite to the first thickness direction, and an edge surface which is continuous between the first outer surface and the second outer surface, and the edge surface includes a blade portion.

7. The ultrasonic probe according to claim 6, wherein the edge surface includes a first side edge facing in a first width direction which is one of the width directions, a second side edge facing in a second width direction which is opposite to the first width direction, and a distal edge which faces in the distal direction and which forms the distal end of the ultrasonic probe.

8. The ultrasonic probe according to claim 1, wherein a first longitudinal dimension of the width dimension decrease portion in the longitudinal directions is larger than a second longitudinal dimension of the intermediary portion in the longitudinal directions.

9. An ultrasonic treatment instrument comprising:
the ultrasonic probe according to claim 1; and
a vibration generator which is configured to generate the ultrasonic vibration to be transmitted to the ultrasonic probe by a supply of an ultrasonic generating electric power.

* * * * *